(12) United States Patent
Uehara

(10) Patent No.: US 11,168,042 B2
(45) Date of Patent: Nov. 9, 2021

(54) SYSTEMS AND METHODS FOR ISOPRENE PURIFICATION

(71) Applicant: SABIC Global Technologies B.V., Bergen op Zoom (NL)

(72) Inventor: Ernesto Uehara, Riyadh (SA)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 16/604,278

(22) PCT Filed: Apr. 12, 2018

(86) PCT No.: PCT/IB2018/052562
§ 371 (c)(1),
(2) Date: Oct. 10, 2019

(87) PCT Pub. No.: WO2018/207038
PCT Pub. Date: Nov. 15, 2018

(65) Prior Publication Data
US 2020/0055802 A1 Feb. 20, 2020

Related U.S. Application Data

(60) Provisional application No. 62/504,246, filed on May 10, 2017.

(51) Int. Cl.
*C07C 7/167* (2006.01)
*C07C 11/18* (2006.01)

(52) U.S. Cl.
CPC .............. *C07C 7/167* (2013.01); *C07C 11/18* (2013.01)

(58) Field of Classification Search
CPC ............ C07C 7/163; C07C 7/167; C07C 5/08; C07C 11/18
See application file for complete search history.

(56) References Cited

U.S. PATENT DOCUMENTS 2,851,505 A * 9/1958 Henke ................... C07C 11/18
203/70
2,935,540 A 5/1960 Wolfe et al. .................. 585/810
(Continued)

FOREIGN PATENT DOCUMENTS

WO WO2010070030 A2 6/2010

OTHER PUBLICATIONS

Dow (https://www.dow.com/ content/dam/dcc/documents/en-us/productdatasheet/778/778-01801-01-c-5-dienes-crude-tds.pdf?iframe=true; Published Jun. 2014) (Year: 2014).*
(Continued)

*Primary Examiner* — Youngsul Jeong
*Assistant Examiner* — Jason Y Chong
(74) *Attorney, Agent, or Firm* — Norton Rose Fulbright US LLP

(57) ABSTRACT

Methods for the selective hydrogenation of acetylenic compounds in a product stream that includes isoprene. A method of selectively hydrogenating an acetylenic hydrocarbon in the presence of isoprene may include obtaining a hydrocarbon mixture comprising an acetylenic hydrocarbon, isoprene, and butadiene or cyclopentadiene, or both. If cyclopentadiene is present, the hydrocarbon mixture may comprise greater than 2 wt. % cyclopentadiene. The method may further include contacting the hydrocarbon mixture and hydrogen ($H_2$) with a hydrogenation catalyst under reaction conditions that are more selective to the hydrogenation of the acetylenic hydrocarbon than the isoprene.

15 Claims, 2 Drawing Sheets

(56) References Cited

U.S. PATENT DOCUMENTS

| | | | | |
|---|---|---|---|---|
| 3,075,025 | A | | 1/1963 | Henke et al. ................ 585/860 |
| 3,541,178 | A | * | 11/1970 | Nettesheim ............ C07C 7/167 |
| | | | | 585/262 |
| 3,555,106 | A | | 1/1971 | Ohmori ..................... 260/681.5 |
| 3,922,318 | A | | 11/1975 | Martino et al. ............... 585/261 |
| 6,127,588 | A | | 10/2000 | Kimble et al. ................ 585/260 |
| 6,169,218 | B1 | * | 1/2001 | Hearn .................... C10G 45/32 |
| | | | | 585/260 |
| 6,437,206 | B1 | | 8/2002 | Meyer et al. ................. 585/260 |
| 6,958,426 | B2 | | 10/2005 | Tian et al. ................... 585/329 |
| 8,637,719 | B2 | | 1/2014 | Fischer et al. ............... 585/250 |
| 2006/0025641 | A1 | | 2/2006 | Gartside et al. ............ 585/260 |
| 2017/0362145 | A1 | * | 12/2017 | Van Der Waal ........ C07C 29/60 |

OTHER PUBLICATIONS

International Search Report and Written Opinion from PCT/IB2018/052562 dated Jul. 16, 2018, 9 pages.

* cited by examiner

SYSTEMS AND METHODS FOR ISOPRENE PURIFICATION

CROSS REFERENCE TO RELATED APPLICATIONS

This application is a national phase application under 35 U.S.C. § 371 of International Application No. PCT/IB2018/052562 filed Apr. 12, 2018, which claims priority to U.S. Provisional Patent Application No. 62/504,246 filed May 10, 2017. The entire contents of each of the above-referenced disclosures is specifically incorporated by reference herein without disclaimer.

FIELD OF INVENTION

The present invention generally relates to the purification of isoprene. More specifically, the present invention relates to the selective hydrogenation of acetylenic compounds in a product stream that includes isoprene.

BACKGROUND OF THE INVENTION

Isoprene ($CH_2$=C($CH_3$)—CH=$CH_2$) is an important petrochemical. It is used, for example, in the production of rubbers and plastics. Isoprene is typically produced as a byproduct of hydrocarbon pyrolysis or hydrocarbon catalytic cracking to produce ethylene. From the pyrolysis process or the catalytic process, the isoprene is usually in a product mixture that also includes $C_4$ and $C_5$ hydrocarbons, which includes acetylenic $C_4$ and $C_5$ hydrocarbons). These acetylenic hydrocarbons can present detrimental effects on downstream processes. Thus, there is a need to separate the acetylenic compounds from the isoprene before the isoprene can be used in other processes. However, the volatility of isoprene and the other acetylenic hydrocarbons are similar. This makes separation by distillation difficult. Thus, extractive distillation employed for the separation of acetylenic compounds from isoprene is typically elaborate and expensive.

Selective hydrogenation in the presence of catalysts containing noble metals is one method of separating isoprene from acetylenic hydrocarbons (e.g., the selective hydrogenation of vinyl acetylene for butadiene production). However, the selective hydrogenation process, depending on how it is implemented, can result in extensive loss of diolefins, such as isoprene.

BRIEF SUMMARY OF THE INVENTION

A method has been discovered for the selective hydrogenation of acetylenic compounds in a product stream that includes isoprene. The method implements operating conditions (e.g., temperature, pressure, weight hourly space velocity (WHSV)) that minimize the loss of isoprene in the hydrogenation process.

Embodiments of the invention include a method of selectively hydrogenating an acetylenic hydrocarbon in the presence of isoprene. The method includes obtaining a hydrocarbon mixture comprising an acetylenic hydrocarbon, isoprene, and butadiene or cyclopentadiene, or both. The hydrocarbon mixture may comprise greater than 2 wt. % cyclopentadiene, if present. Embodiments of the invention may further include contacting the hydrocarbon mixture and hydrogen ($H_2$) with a hydrogenation catalyst under reaction conditions that are more selective to the hydrogenation of the acetylenic hydrocarbon than the isoprene.

The following includes definitions of various terms and phrases used throughout this specification.

The terms "about" or "approximately" are defined as being close to as understood by one of ordinary skill in the art. In one non-limiting embodiment the terms are defined to be within 10%, preferably, within 5%, more preferably, within 1%, and most preferably, within 0.5%.

The terms "wt. %", "vol. %" or "mol. %" refers to a weight, volume, or molar percentage of a component, respectively, based on the total weight, the total volume, or the total moles of material that includes the component. In a non-limiting example, 10 moles of component in 100 moles of the material is 10 mol. % of component.

The term "substantially" and its variations are defined to include ranges within 10%, within 5%, within 1%, or within 0.5%.

The terms "inhibiting" or "reducing" or "preventing" or "avoiding" or any variation of these terms, when used in the claims and/or the specification, includes any measurable decrease or complete inhibition to achieve a desired result.

The term "effective," as that term is used in the specification and/or claims, means adequate to accomplish a desired, expected, or intended result.

The use of the words "a" or "an" when used in conjunction with the term "comprising," "including," "containing," or "having" in the claims or the specification may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The process of the present invention can "comprise," "consist essentially of," or "consist of" particular ingredients, components, compositions, etc., disclosed throughout the specification.

In the context of the present invention, at least sixteen embodiments are now described. Embodiment 1 is a method of selectively hydrogenating an acetylenic hydrocarbon in the presence of isoprene, the method including the steps of (a) obtaining a hydrocarbon mixture containing an acetylenic hydrocarbon, isoprene, and butadiene or cyclopentadiene, or both, wherein, the hydrocarbon mixture contains greater than 2 wt. % cyclopentadiene, if present; and (b) contacting the hydrocarbon mixture and hydrogen H2) with a hydrogenation catalyst under reaction conditions that are more selective to the hydrogenation of the acetylenic hydrocarbon than the isoprene. Embodiment 2 is the method of embodiment 1, wherein the hydrogenation catalyst contains nickel (Ni), palladium (Pd), or platinum (Pt), or combinations or alloys thereof. Embodiment 3 is the method of any of embodiments 1 and 2, wherein less than 10% of the isoprene is hydrogenated. Embodiment 4 is the method of any of embodiments 1 to 3, wherein the acetylenic hydrocarbon is butyne, preferably 2-butyne. Embodiment 5 is the method of any of embodiments 1 to 4, wherein the reaction conditions include a temperature in a range of 30 to 50° C. Embodiment 6 is the method of any of embodiments 1 to 5, wherein the reaction conditions include a pressure in a range of less than 10 bar(g), preferably 5 to 8 bar(g). Embodiment 7 is the method of any of embodiments 1 to 6, wherein the reaction conditions include a weight hourly space velocity (WHSV) in a range of 1 to 4 h-1. Embodiment 8 is the method of any of embodiments 1 to 7, wherein the reaction conditions include a mol. % ratio of H2/butyne of 2 to 3. Embodiment 9 is the method of any of embodiments 1 to 8, wherein the amount of cyclopentadiene in the hydrocarbon mixture is 5 to 25 wt. %. Embodiment 10 is the method of any of embodiments 1 to 9, wherein the hydrocarbon mixture is a liquid. Embodiment 11 is the method of any of embodiments 1 to 10, wherein there is a complete hydrogenation of the acetylenic hydrocarbon. Embodiment 12 is the method of any of embodiments 1 to 11, wherein, the method does not include a dimerization reaction involving cyclopentadiene. Embodiment 13 is the method of any of embodiments 1 to 12, wherein the butadiene is added to a product stream from a pyrolysis or cracking process to form the hydrocarbon mixture. Embodiment 14 is the method of any of embodiments 1 to 13, wherein the cyclopentadiene is added to a product stream from a pyrolysis or cracking process to form the hydrocarbon mixture. Embodiment 15 is the method of any of embodiments 1 to 14, wherein the contacting occurs in a fixed-bed reactor.

Embodiment 16 is a method of selectively hydrogenating butyne in the presence of isoprene, the method including the steps of (a) obtaining a hydrocarbon mixture containing butyne, isoprene, butadiene, and cyclopentadiene, wherein, the hydrocarbon mixture contains 3 wt. % to 25 wt. % cyclopentadiene; and (b) contacting the hydrocarbon mixture and hydrogen (H2) with a hydrogenation catalyst containing nickel (Ni), palladium (Pd), or platinum (Pt), or combinations or alloys thereof, in a fixed bed reactor at a temperature of less than 80° C., a pressure less than 10 bar(g), and a weight hour space velocity (WHSV) of less than 8 h-1, under reaction conditions such that less than 7% of the isoprene is hydrogenated, wherein the mol. % ratio of H2:butyne is less than 6:1.

Other objects, features and advantages of the present invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description. In further embodiments, features from specific embodiments may be combined with features from other embodiments. For example, features from one embodiment may be combined with features from any of the other embodiments. In further embodiments, additional features may be added to the specific embodiments described herein.

BRIEF DESCRIPTION OF THE DRAWINGS

For a more complete understanding, reference is now made to the following descriptions taken in conjunction with the accompanying drawings, in which.

DETAILED DESCRIPTION OF THE INVENTION

A method has been discovered for the selective hydrogenation of acetylenic compounds in a product stream that includes isoprene. The method implements operating conditions (e.g., temperature, pressure, weight hourly space velocity (WHSV)) that minimize the loss of isoprene in the hydrogenation process.

Embodiments of the invention include a method of selectively hydrogenating an acetylenic hydrocarbon (e.g., 2-butyne, $CH_3-C\equiv C-CH_3$) in the presence of isoprene. The method includes obtaining a hydrocarbon mixture comprising an acetylenic hydrocarbon, isoprene, and butadiene or cyclopentadiene, or both. The hydrocarbon mixture may include greater than 2 wt. % cyclopentadiene, if present. Embodiments of the invention may further include contacting the hydrocarbon mixture and hydrogen ($H_2$) with a hydrogenation catalyst under reaction conditions that are more selective to the hydrogenation of the acetylenic hydrocarbon than the isoprene.

Figure 1:
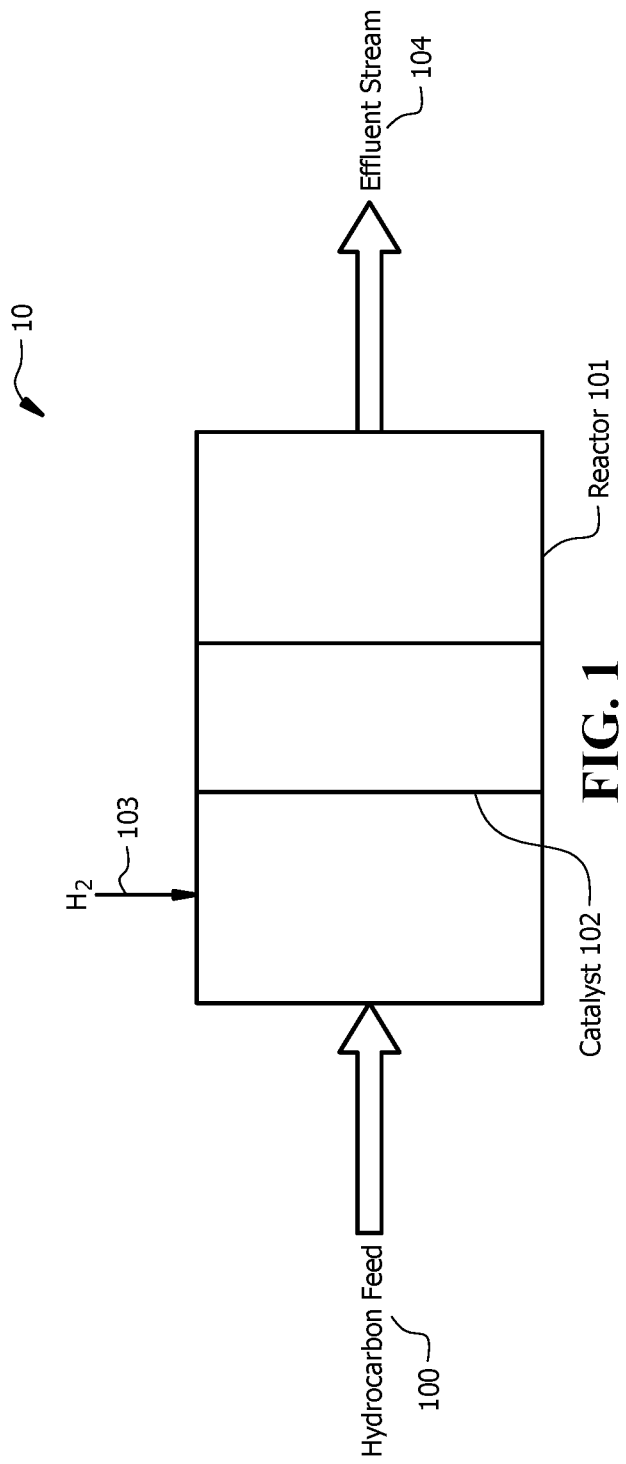
FIG. 1 shows a system for the selective hydrogenation of acetylenic compounds in presence of isoprene, according to embodiments of the invention.
Figure 2:
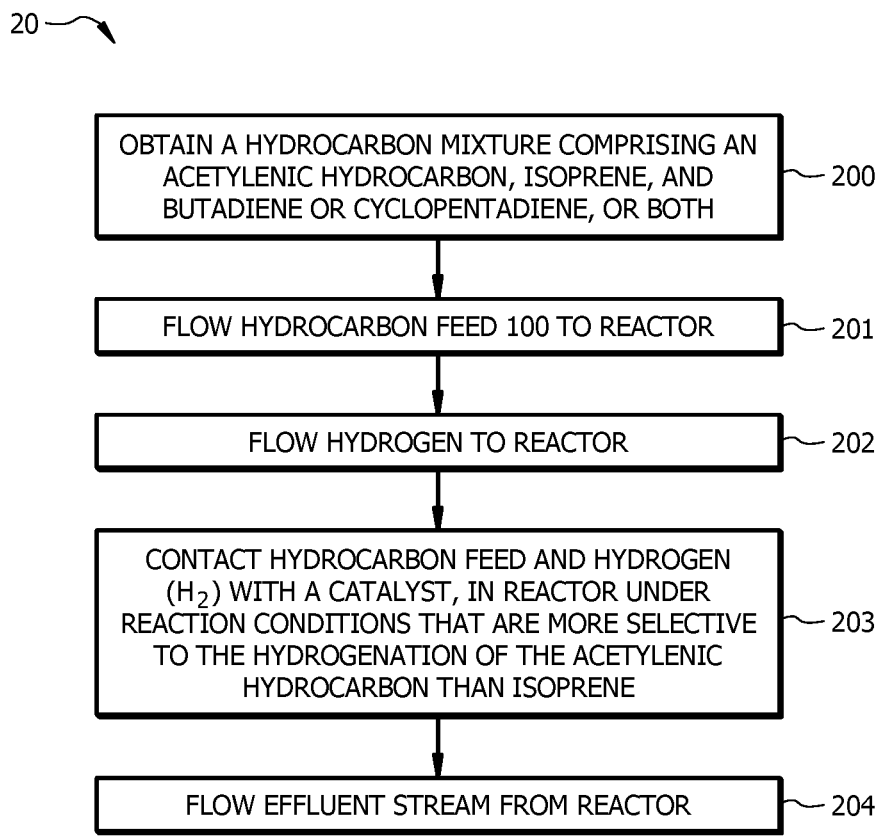
FIG. 2 shows a method for the selective hydrogenation of acetylenic compounds in presence of isoprene, according to embodiments of the invention.

FIG. 1 shows system 10 for the selective hydrogenation of acetylenic compounds in presence of isoprene, according to embodiments of the invention. FIG. 2 shows method 20 for the selective hydrogenation of acetylenic compounds in presence of isoprene, according to embodiments of the invention. Method 20 may be implemented with system 10. Embodiments of the invention, as illustrated in FIG. 1, include the selective hydrogenation of components of hydrocarbon feed 100. Hydrocarbon feed 100 may be a $C_4$ cut (fraction) and/or a $C_5$ cut from a catalytic cracking process, for example, that produces ethylene. According to embodiments of the invention, hydrocarbon feed 100 is a mixture of different compounds, including isoprene and acetylenic compounds (e.g., $C_4$ and/or $C_5$ acetylenic compounds). In embodiments of the invention, cyclopentadiene may be present with the isoprene in hydrocarbon feed 100 as a byproduct of hydrocarbon pyrolysis. Alternatively or additionally, cyclopentadiene may be added to a product stream (e.g., a product stream from a pyrolysis or cracking process) to form hydrocarbon feed 100, as it is theorized that the presence of cyclopentadiene may help in the minimization of isoprene loss in the hydrogenation process. Similarly, it is theorized that the presence of butadiene may help in the minimization of isoprene loss in the hydrogenation process. In view of this, butadiene may also be added to a product stream (e.g., a product stream from a pyrolysis or cracking process) to form hydrocarbon feed 100 to minimize such isoprene loss in the hydrogenation process. Thus, hydrocarbon feed 100 may include one or more acetylenic hydrocarbons, isoprene, and butadiene or cyclopentadiene ($C_5H_6$), or both. In embodiments of the invention in which cyclopentadiene is present, hydrocarbon feed 100 may include greater than 2 wt. % cyclopentadiene. Further, in embodiments of the invention, the amount of cyclopentadiene in the hydrocarbon mixture is 5 to 25 wt. %. Hydrocarbon feed 100 may include 3 wt. % to 25 wt. % cyclopentadiene. In embodiments of the invention, hydrocarbon feed 100 is a liquid.

Consistent with the foregoing, method 20 may include, at block 200, obtaining a hydrocarbon mixture (e.g., hydrocarbon feed 100) comprising an acetylenic hydrocarbon, isoprene, and butadiene or cyclopentadiene, or both. The hydrocarbon mixture may include greater than 2 wt. % cyclopentadiene, if present. Obtaining this hydrocarbon mixture may include adding butadiene and/or cyclopentadiene to a hydrocarbon stream that includes isoprene. At block 201, method 20 may then include flowing hydrocarbon feed 100 to reactor 101 (FIG. 1). In embodiments of the invention, reactor 101 may be a fixed-bed reactor configured to hydrogenate particular components of hydrocarbon feed 100.

For example, reactor 101, as shown in FIG. 1, includes catalyst 102. Catalyst 102 may be a hydrogenation catalyst adapted to selectively hydrogenate acetylenic compounds. Catalyst 102 may be a selection from: nickel (Ni) catalyst, palladium (Pd) catalyst, platinum (Pt) catalyst, alloys thereof, and combinations thereof. According to embodiments of the invention, catalyst 102 selectively hydrogenates acetylenic compounds due to the much stronger adsorption of these compounds by catalyst 102, as compared to other compounds of hydrocarbon feed 100. These acetylenic compounds, in embodiments of the invention, stay adsorbed on catalyst 102 until complete saturation. Active sites of catalyst 102 available for hydrogen adsorption are different from those available for adsorption of acetylenics compounds. Because acetylenic compounds having triple bonds are more reactive than diolefins having double bonds, short contact time may allow complete hydrogenation of the acetylenic compounds before saturation of diolefins. According to embodiments of the invention, there is no direct competition between hydrogen and the acetylenic compounds for the same sites because hydrogen molecules are so small that they can find free sites even though the catalytic surface is completely covered by the strongly adsorbed acetylenic compounds.

In embodiments of the invention, method 20 may include, at block 202, flowing hydrogen to reactor 101. With hydrogen present, method 20, at block 203, may involve contacting hydrocarbon feed 100 and hydrogen ($H_2$) with catalyst 102, in reactor 101 under reaction conditions that are more selective to the hydrogenation of the acetylenic hydrocarbon than isoprene.

In embodiments of the invention, the reaction conditions within reactor 101 for the selective hydrogenation of acetylenic hydrocarbons may include a temperature in a range of less than 80° C., and all ranges and values therein including ranges 0 to 5° C., 5 to 10° C., 10 to 15° C., 15 to 20° C., 20 to 25° C., 25 to 30° C., 30 to 35° C., 35 to 40° C., 40 to 45° C., 45 to 50° C., 50 to 55° C., 55 to 60° C., 60 to 65° C., 65 to 70° C., 70 to 75° C., and 75 to 80° C., preferably 30 to 50° C. With respect to pressure, the reaction conditions within reactor 101 for the selective hydrogenation of acetylenic hydrocarbons may include a pressure in the range of less than 10 bar(g), and all ranges and values therein including ranges 1 to 2 bar(g), 2 to 3 bar(g), 3 to 4 bar(g), 4 to 5 bar(g), 5 to 6 bar(g), 6 to 7 bar(g), 7 to 8 bar(g), 8 to 9 bar(g), and 9 to 10 bar(g), preferably 5 to 8 bar(g), and values of 1 bar(g), 2 bar(g), 3 bar(g), 4 bar(g), 5 bar(g), 6 bar(g), 7 bar(g), 8 bar(g), 9 bar(g), and 10 bar(g). And with respect to weight hourly space velocity (WHSV), the reaction conditions within reactor 101 for the selective hydrogenation of acetylenic hydrocarbons may include a WHSV in a range less than 8 $h^{-1}$, and all ranges and values therein including ranges 1 to 2 $h^{-1}$, 2 to 3 $h^{-1}$, 3 to 4 $h^{-1}$, 4 to 5 $h^{-1}$, 5 to 6 $h^{-1}$, 6 to 7 $h^{-1}$, and 7 to 8 $h^{-1}$, and values 1 $h^{-1}$, 2 $h^{-1}$, 3 $h^{-1}$, 4 $h^{-1}$, 5 $h^{-1}$, 6 $h^{-1}$, 7 $h^{-1}$, and 8 $h^{-1}$, preferably 1 to 4 $h^{-1}$. In embodiments of the invention in which butyne is present, the reaction conditions may include a mol. % ratio of $H_2$/butyne of less than 6 mol. %, and all ranges and values therein including ranges of 1 to 2 mol. %, 2 to 3 mol. %, 3 to 4 mol. %, 4 to 5 mol. %, and 5 to 6 mol. %, and values of 1 mol. %, 2 mol. %, 3 mol. %, 4 mol. %, 5 mol. %, and 6 mol. %, preferably 2 to 3 mol. %.

According to embodiments of the invention, under the reaction conditions of reactor 101, acetylenic compounds of hydrocarbon feed 100 is hydrogenated and effluent stream 104 is flowed from reactor 101, at block 204.

In embodiments of the invention the acetylenic hydrocarbons of hydrocarbon feed 100 are completely hydrogenated. In embodiments of the invention, method 20 does not include a dimerization reaction involving cyclopentadiene. In embodiments of the invention, less than 10% of the isoprene is hydrogenated. In embodiments of the invention, the acetylenic hydrocarbons can be butyne, preferably 2-butyne, or combinations thereof. In embodiments of the invention, less than 7% of the isoprene is hydrogenated, wherein the mol. % ratio of $H_2$:butyne is less than 6:1.

Although embodiments of the present application and their advantages have been described in detail, it should be understood that various changes, substitutions and alterations can be made herein without departing from the spirit and scope of the embodiments as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the above disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

The invention claimed is:

1. A method of selectively hydrogenating an acetylenic hydrocarbon wherein isoprene is present, the method comprising the steps of:
   (a) obtaining a hydrocarbon mixture comprising (i) an acetylenic hydrocarbon, (ii) isoprene, and (iii) at least one member selected from the group consisting of butadiene and cyclopentadiene, wherein the hydrocarbon mixture comprises greater than 2 wt. % cyclopentadiene, if present; and
   (b) contacting in a reactor the hydrocarbon mixture and hydrogen ($H_2$) with a hydrogenation catalyst comprising platinum under reaction conditions that are more selective to hydrogenation of the acetylenic hydrocarbon than the isoprene to produce an effluent comprising a hydrogenated compound;
   wherein the reaction conditions within the reactor for the selective hydrogenation of acetylenic hydrocarbons include a pressure in a range of from 1 to 10 bar(g) and a temperature in a range of from 55 to 80° C.

2. The method of claim 1, wherein less than 10% of the isoprene is hydrogenated.

3. The method of claim 1, wherein the acetylenic hydrocarbon is butyne.

4. The method of claim 1, wherein the pressure is in a range of 5 to 8 bar(g).

5. The method of claim 1, wherein the acetylenic hydrocarbon is 2-butyne.

6. The method of claim 1, wherein an amount of cyclopentadiene in the hydrocarbon mixture is 15 to 25 wt. %.

7. The method of claim 1, wherein the reaction conditions include a weight hourly space velocity (WHSV) is 1 $h^{-1}$.

8. The method of claim 1, wherein the method does not include a dimerization reaction involving cyclopentadiene.

9. The method of claim 1, wherein the butadiene is added to a product stream from a pyrolysis or cracking process to form the hydrocarbon mixture.

10. The method of claim 1, wherein the cyclopentadiene is added to a product stream from a pyrolysis or cracking process to form the hydrocarbon mixture.

11. The method of claim 1, wherein the contacting occurs in a fixed-bed reactor.

12. The method of claim 1, wherein the acetylenic hydrocarbon is butyne wherein the hydrocarbon mixture comprises 3 wt. % to 25 wt. % cyclopentadiene; wherein the reactor is a fixed bed reactor, wherein the reaction conditions within the reactor include a temperature of 75° C. to 80° C., and a weight hour space velocity (WHSV) of less than 8 $h^{-1}$, under reaction conditions such that less than 7% of the isoprene is hydrogenated to produce an effluent comprising a hydrogenated compound.

13. The method of claim 12, wherein a molar ratio of $H_2$:butyne is less than 6:1.

14. The method of claim 1 wherein the reaction conditions include a temperature of 80° C.

15. The method of claim 1, wherein the cyclopentadiene is present and wherein the amount of the cyclopentadiene in the hydrocarbon mixture is 10 to 25 wt. %.

\* \* \* \* \*